United States Patent
Lucet-Levannier

(10) Patent No.: US 7,795,286 B2
(45) Date of Patent: Sep. 14, 2010

(54) SILANE ESTERS AND AMIDES OF 2-OXOTHIAZOLIDINE-4-CARBOXYLIC ACID, AND COSMETIC USES THEREOF

(75) Inventor: Karine Lucet-Levannier, Reuil-Malmaison (FR)

(73) Assignee: L'Oreal, Paris (FR)

( * ) Notice: Subject to any disclaimer, the term of this patent is extended or adjusted under 35 U.S.C. 154(b) by 613 days.

(21) Appl. No.: 11/577,600

(22) PCT Filed: Sep. 27, 2005

(86) PCT No.: PCT/EP2005/012032

§ 371 (c)(1),
(2), (4) Date: Nov. 9, 2007

(87) PCT Pub. No.: WO2006/045639

PCT Pub. Date: May 4, 2006

(65) Prior Publication Data

US 2009/0074682 A1    Mar. 19, 2009

Related U.S. Application Data

(60) Provisional application No. 60/632,541, filed on Dec. 3, 2004.

(30) Foreign Application Priority Data

Oct. 21, 2004   (FR) .................................. 04 52399

(51) Int. Cl.
| A61K 31/695 | (2006.01) |
| A61K 31/425 | (2006.01) |
| A61K 8/18 | (2006.01) |
| A61Q 19/00 | (2006.01) |
| A61Q 19/08 | (2006.01) |
| C07D 231/08 | (2006.01) |
| A01N 55/00 | (2006.01) |
| A01N 43/78 | (2006.01) |

(52) U.S. Cl. ............................ 514/369; 424/59; 514/63; 514/365; 548/110

(58) Field of Classification Search ....................... None
See application file for complete search history.

(56) References Cited

FOREIGN PATENT DOCUMENTS

| EP | 0 583 863 | 2/1994 |
| EP | 1 471 067 | 10/2004 |

*Primary Examiner*—Ernst V Arnold
(74) *Attorney, Agent, or Firm*—Oblon, Spivak, McClelland, Maier & Neustadt, L.L.P.

(57) ABSTRACT

The present invention relates to novel compounds of formula (1) and also to cosmetic compositions containing them and to the cosmetic uses thereof, in particular for protecting the skin against UV-induced oxidative stress.

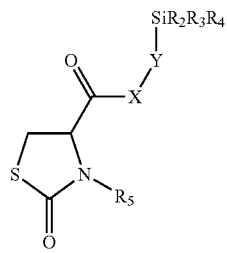

19 Claims, No Drawings

SILANE ESTERS AND AMIDES OF 2-OXOTHIAZOLIDINE-4-CARBOXYLIC ACID, AND COSMETIC USES THEREOF

This application is a 371 of PCT/EP05/12032 filed on Sep. 27, 2005 which claims priority to provisional application 60/632,541 filed on Dec. 3, 2004 and claims foreign priority to France 0452399 filed on Oct. 21, 2004.

The present invention relates to novel silane esters and amides of 2-oxothiazolidine-4-carboxylic acid, to cosmetic compositions containing them and to the cosmetic uses thereof.

The harmful effects caused by exposure of the skin to sunlight are now well known. It is thus known that UVB is responsible for erythema and impairments of epidermal cells, which can form malignant tumours in the more or less long term, while UVA is responsible for the vast majority of solar allergies and of oxidative damage on account of its capacity to form activated oxygen species, which are capable of reacting especially with cell membranes.

To protect the skin against the effects of UV, it is standard practice to incorporate into cosmetic products UVA- and UVB-screening agents that absorb the energy provided by the photons or scatter light, and also free-radical scavengers to combat the skin damage caused by the free radicals generated by the UV radiation. However, these measures are not entirely sufficient to protect the skin against the harmful effects of UV.

Compounds such as glutathione and precursors thereof have thus been proposed, which make it possible to reduce the effects of oxidative stress at the cellular level. These compounds induce active photoprotection by stimulating the natural defense systems of the skin cells against the damage induced by UV radiation.

Procysteine or 2-oxothiazolidine-4-carboxylic acid is an example of a compound that stimulates the synthesis of reduced glutathione. This compound and its esters have already been described as being useful for protecting the body against various types of stress (U.S. Pat. No. 4,335,210; U.S. Pat. No. 4,434,158; U.S. Pat. No. 4,438,124 and U.S. Pat. No. 4,467,751), for combating hair loss (EP-0 656 201), as depigmenting agents (EP-0 780 120) or as desquamating agents (FR-2 816 838).

However, there is still a need for compounds that are more efficient than procysteine in maintaining the intracellular redox equilibrium.

The Applicant has now discovered, surprisingly and unexpectedly, that certain procysteine derivatives, more specifically silane esters and amides of 2-oxothiazolidine-4-carboxylic acid, make it possible to satisfy this need, thus making it possible to envisage their use in the photoprotection of the skin and the prevention of photoageing of the skin. These compounds are also of interest in preventing skin pigmentation, in particular UV-induced pigmentation. To the Applicant's knowledge, these compounds have never yet been described.

One subject of the present invention is thus novel compounds of formula (I):

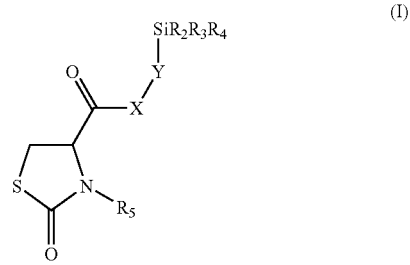

in which:
X denotes an oxygen atom or a group $NR_1$;
Y denotes a radical $(-CH_2)_n-$ or $-CH-(SiR'_2R'_3R'_4)-$;
$R_1$ and $R_5$ independently denote a hydrogen atom; a linear or branched $C_1$-$C_{20}$ alkyl group; or an acyl group whose alkyl chain contains from 1 to 10 carbon atoms;
$R_2$, $R_3$, $R_4$, $R'_2$, $R'_3$ and $R'_4$ independently denote a linear or branched $C_1$-$C_{20}$ alkyl group;
n is an integer ranging from 1 to 10.

Alkyl groups that may be mentioned include methyl, ethyl, propyl, isopropyl, butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups.

Acyl groups that may be mentioned in particular include acetyl, propionyl and butanoyl groups.

The compounds of formula (I) may be in the form of optically pure isomers (S or R form) or in the form of a mixture thereof in any proportion, in particular a racemic mixture. For the purposes of this invention, the compounds of formula (I) that are in the form of the R (or L) isomer are preferred.

Among these compounds, the ones that are most particularly preferred are those for which:
X is an oxygen atom or a group $NR_1$, in which $R_1$ denotes a $C_1$-$C_3$ alkyl radical or, preferably, a hydrogen atom; and/or
$R_2$, $R_3$ and $R_4$ are identical or different $C_1$-$C_3$ alkyl radicals; and/or
$R'_2$, $R'_3$ and $R'_4$ are identical or different $C_1$-$C_3$ alkyl radicals or n is an integer ranging from 1 to 3; and/or
$R_5$=H.

$C_1$-$C_3$ alkyl radicals that may be mentioned include methyl, ethyl, propyl and isopropyl groups.

The compound that is preferred according to the present invention is the one for which X is an oxygen atom: n=1; $R_2$=$R_3$=$R_4$=$CH_3$; and $R_5$=H.

This is methyltrimethylsilyl R-2-oxo-1,3-thiazolidine-4-carboxylate of formula (1):

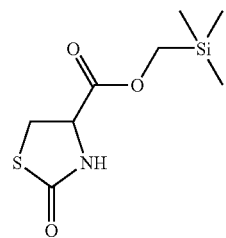

Other compounds that are suitable for use in the present invention may be chosen from:
(4R)-2-oxo-N-[(trimethylsilyl)methyl]-1,3-thiazolidine-4-carboxamide of formula (2):

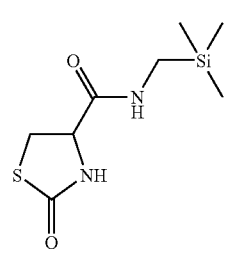

(4R)-N-[bis(trimethylsilyl)methyl]-2-oxo-1,3-thiazolidine-4-carboxamide of formula (3):

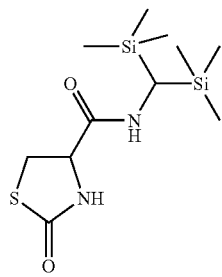

(3)

2-(trimethylsilyl)ethyl(4R)-2-oxo-1,3-thiazolidine-4-carboxylate of formula (4):

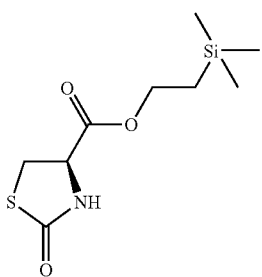

(4)

3-(trimethylsilyl)propyl(4R)-2-oxo-1,3-thiazolidine-4-carboxylate of formula (5):

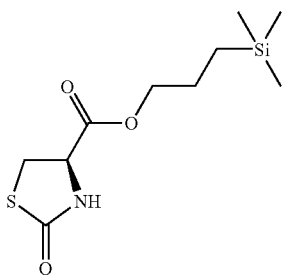

(5)

The compounds in which X is an oxygen atom may be prepared according to a standard esterification reaction between the 2-oxothiazolidine carboxylate obtained in basic medium (for example by reacting with $K_2CO_3$ in N-methylpyrrolidone or dimethylformamide) and a corresponding alkylsilane halide, or alternatively between the 2-oxothiazolidine-4-carboxylic acid and the corresponding silyl alcohol, by analogy with the processes described in Example 1 below.

The compounds in which X is a group $NR_1$ or O may be prepared in a standard manner, by activation of 2-oxothiazolidine-4-carboxylic acid in acyl chloride form (for example in dichloromethane or dimethyl-formamide) or in N-succinimidyl form (for example in the presence of EDCl and diisopropylamine in acetonitrile) followed by reaction of the activated species with the amine or the alcohol bearing the desired silyl group. These reactions are preferably performed under an inert atmosphere and in anhydrous medium. This process is illustrated in Examples 2 to 4 below.

These synthetic processes may be performed using starting materials in enantiomerically pure form or in racemic form. Specifically, 2-oxothiazolidine-4-carboxylic acid is commercially available in racemic form or in R form and may be obtained in S form by chemical synthesis, according to the procedure described in the publication Methods in Enzymology, Vol. 113, pp 458-460, using the S enantiomer of cysteine.

The compound of formula (I) is mainly intended for caring for or treating the skin, in particular the face, the neck, the hands and the neckline. It may also be intended for application to the entire body, in particular when it is incorporated into an antisun product. This compound is thus generally conveyed in a composition suitable for topical application to the skin.

A subject of the present invention is thus also a composition suitable for topical application to the skin, comprising a compound of formula (I) in a physiologically acceptable medium that is compatible with the skin.

The amount of compound of formula (I) according to the invention may represent from 0.001% to 10% and preferably from 0.01% to 5% of the total weight of the composition.

The term "physiologically acceptable medium" means a medium that is compatible with the skin and possibly its integuments. It is preferably a cosmetically acceptable medium, i.e. a medium that has a pleasant colour, odour and feel and that does not cause any unacceptable discomfort (stinging, tautness or redness) liable to put the consumer off using this composition. This medium generally contains water.

The composition according to the invention may be in any galenical form conventionally used for topical application and especially in the form of lotions, emulsions of liquid or semi-liquid consistency of the milk type, obtained by dispersing a fatty phase in an aqueous phase (O/W) or, conversely, (W/O), or suspensions or emulsions of soft, semi-solid or solid consistency of the cream or gel type, or alternatively multiple emulsions (W/O/W or O/W/O), microemulsions, vesicular dispersions of ionic and/or non-ionic type, or wax/aqueous phase dispersions. These compositions are prepared according to the usual methods.

According to one preferred embodiment of the invention, the composition is in the form of an O/W emulsion.

This composition may also contain various adjuvants commonly used in cosmetics, such as emulsifiers, including fatty acid esters of polyoxyethylene, optionally polyethoxylated fatty acid esters of sugars, and fatty acid esters of glycerol; fillers; preserving agents; sequestering agents; dyes; fragrances; and thickeners and gelling agents, in particular acrylamide homopolymers and copolymers, acrylamidomethylpropanesulfonic acid (AMPS) homopolymers and copolymers, and acrylic homopolymers and copolymers.

Needless to say, a person skilled in the art will take care to select this or these optional additional compound(s) and/or the amount thereof such that the advantageous properties of the composition according to the invention are not, or are not substantially, adversely affected by the envisaged addition.

The compound of formula (I) according to the invention makes it possible to protect the skin and the scalp against oxidative stress, by maintaining the intracellular redox balance.

A subject of the present invention is thus also the use of a compound of formula (I) as an agent for preventing photoageing of the skin.

The targeted signs of photoageing of the skin are especially the appearance of wrinkles and fine lines and pigmentation marks, yellowing of the skin (which develops a weathered look), disorganization of the elastin and collagen fibres, resulting in a loss of elasticity, suppleness and firmness of the skin, and the appearance of telangiectasias.

A subject of the present invention is thus in particular the use of a compound of formula (I) for preventing or reducing wrinkles and fine lines and slackening of the skin.

A subject of the present invention is also the use of a compound of formula (I) for preventing UV-induced pigmentation of the skin.

The compounds according to the invention are useful in particular for preparing the skin to receive sunlight or for protecting the skin during exposure to UV.

A subject of the invention is also a cosmetic process for preventing photoageing of the skin, comprising the topical application to the skin of a composition comprising a compound of formula (I) in a physiologically acceptable medium.

To reinforce or complement the abovementioned effects of the composition according to the invention, it may contain at least one compound chosen from: moisturizers; anti-pollution agents or free-radical scavengers; and soothing agents. These additional active agents will now be described in greater detail.

Moisturizers

The term "moisturizer" means:
either a compound acting on the barrier function, in order to maintain the moisturization of the stratum corneum, or an occlusive compound. Mention may be made of ceramides, sphingoid-based compounds, lecithins, glycosphingolipids, phospholipids, cholesterol and its derivatives, phytosterols (stigmasterol, β-sitosterol or campesterol), essential fatty acids, 1,2-diacyl-glycerol, 4-chromanone, pentacyclic triterpenes such as ursolic acid, petroleum jelly and lanolin;

or a compound that directly increases the water content of the stratum corneum, such as threalose and its derivatives, hyaluronic acid and its derivatives, glycerol, pentanediol, sodium pidolate, serine, xylitol, sodium lactate, polyglyceryl acrylate, ectoin and its derivatives, chitosan, oligosaccharides and polysaccharides, cyclic carbonates, N-lauroyl-pyrrolidonecarboxylic acid and N-α-benzoyl-L-arginine;

or a compound that activates the sebaceous glands, such as steroid derivatives (such as DHEA, its 7-oxide and/or 17-alkyl derivatives and sapogenins) and vitamin D and its derivatives.

Anti-Pollution Agents or Free-Radical Scavengers

The term "anti-pollution agent" means any compound capable of trapping ozone, monocyclic or polycyclic aromatic compounds such as benzopyrene and/or heavy metals such as cobalt, mercury, cadmium and/or nickel. The term "free-radical scavenger" means any compound capable of trapping free radicals.

As ozone-trapping agents that may be used in the composition according to the invention, mention may be made in particular of vitamin C and its derivatives including ascorbyl glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chlorogenic acid; stilbenes, in particular resveratrol; sulfur-containing amino acid derivatives, in particular S-carboxymethylcysteine; ergothioneine; N-acetyl-cysteine; chelating agents, for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenylalanine, tyrosine and hydrolysed RNA, sold by the Laboratoires Sérobiologiques under the trade name CPP LS 2633-12F®, the water-soluble fraction of corn sold by the company Solabia under the trade name Phytovityl®, the mixture of extract of fumitory and of extract of lemon sold under the name Unicotrozon C-49® by the company Induchem, and the mixture of extracts of ginseng, of apple, of peach, of wheat and of barley, sold by the company Provital under the trade name Pronalen Bioprotect®.

As agents for trapping monocyclic or polycyclic aromatic compounds, which may be used in the composition according to the invention, mention may be made in particular of tannins such as ellagic acid; indole derivatives, in particular 3-indole-carbinol; extracts of tea, in particular of green tea, extracts of water hyacinth or *Eichhornia crassipes*; and the water-soluble fraction of corn sold by the company Solabia under the trade name Phytovityl®.

Finally, as heavy-metal-trapping agents that may be used in the composition according to the invention, mention may be made in particular of chelating agents such as EDTA, the pentasodium salt of ethylenediaminetetramethylenephosphonic acid, and N,N'-bis(3,4,5-trimethoxybenzyl)ethylenediamine or one of the salts, metal complexes or esters thereof; phytic acid; chitosan derivatives; extracts of tea, in particular of green tea; tannins such as ellagic acid; sulfur-containing amino acids such as cysteine; extracts of water hyacinth (*Eichhornia crassipes*); and the water-soluble fraction of corn sold by the company Solabia under the trade name Phytovityl®.

The free-radical scavengers that may be used in the composition according to the invention comprise, besides certain anti-pollution agents mentioned above, vitamin E and its derivatives such as tocopheryl acetate; bioflavonoids; coenzyme Q10 or ubiquinone; certain enzymes, for instance catalase, superoxide dismutase, lactoperoxidase, glutathione peroxidase and quinone reductases; glutathione; benzylidenecamphor; benzylcyclanones; substituted naphthalenones; pidolates; phytanetriol; gamma-oryzanol; lignans; and melatonin.

Soothing Agents

As soothing agents that may be used in the composition according to the invention, mention may be made of: pentacyclic triterpenes and extracts of plants (e.g.: *Glycyrrhiza glabra*) containing them, for instance β-glycyrrhetinic acid and salts and/or derivatives thereof (glycyrrhetinic acid monoglucuronide, stearyl glycyrrhetinate or 3-stearoyl-oxyglycyrrhetic acid), ursolic acid and its salts, oleanolic acid and its salts, betulinic acid and its salts, extracts of plants such as *Paeonia suffruticosa* and/or *lactiflora, Laminaria saccharina, Boswellia serrata, Centipeda cunnighami, Helianthus annuus, Linum usitatissimum, Cola nitida, Epilobium angustifolium, Aloe vera* or *Bacopa monieri*, salicylic acid salts and in particular zinc salicylate, canola oil, bisabolol and camomile extracts, allantoin, Sepivital EPC (phosphoric diester of vitamins E and C) from SEPPIC, omega-3 unsaturated oils such as musk rose oil, blackcurrant oil, ecchium oil or fish oil, plankton extracts, capryloylglycine, Seppicalm VG (sodium palmitoylproline and *Nymphea alba*) from SEPPIC, tocotrienols, piperonal, an extract of clove, phytosterols, cortisone, hydrocortisone, indomethacin and betamethasone.

The compositions in accordance with the invention may also comprise at least one UVA-active and/or UVB-active organic photoprotective agent and/or at least one UVA-active and/or UVB-active mineral photoprotective agent, which may be water-soluble or liposoluble or even insoluble in the cosmetic solvents commonly used.

The organic photoprotective agents are especially chosen from anthranilates; cinnamic derivatives; dibenzoylmethane derivatives; salicylic derivatives; camphor derivatives; triazine derivatives such as those described in patent applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β'-diphenylacrylate derivatives; benzotriazole derivatives; benzalmalonate derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenyl)benzotriazole derivatives as described in patent applications U.S. Pat. No. 5,237,071, U.S. Pat. No. 5,166, 355, GB 2 303 549, DE 197 26 184 and EP 893 119; benzoxazole derivatives as described in patent-applications EP 0 832 642, EP 1 027 883, EP 1 300 137 and DE 101 62 844; screening polymers and screening silicones such as those described especially in patent application WO 93/04665; dimers derived from α-alkylstyrene such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981, and mixtures thereof.

The organic photoprotective agents that are more particularly preferred are chosen from the following compounds (given as CTFA names or chemical names):

Ethylhexyl salicylate,
Ethylhexyl methoxycinnamate,
Octocrylene,
Phenylbenzimidazolesulfonic acid,
Benzophenone-3,
Benzophenone-4,
Benzophenone-5,
4-Methylbenzylidenecamphor,
Terephthalylidenedicamphorsulfonic acid,
Disodium phenyldibenzimidazoletetrasulfonate,
2,4,6-Tris(diisobutyl 4'-aminobenzalmalonate)-s-triazine,
Anisotriazine,
Ethylhexyltriazone,
Diethylhexylbutamidotriazone,
Methylenebis(benzotriazolyl)tetramethylbutyl-phenol,
Drometrizole trisiloxane,
Polysilicone-15,
1,1-Dicarboxy(2,2'-dimethylpropyl)-4,4-diphenyl-butadiene,
2,4-Bis[5-1(dimethylpropyl)benzoxazol-2-yl(4-phenyl)imino]-6-(2-ethylhexyl)imino-1,3,5-triazine, and mixtures thereof.

The mineral photoprotective agents are chosen from pigments or even nanopigments (mean size of the primary particles: generally between 5 nm and 100 nm and preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminium stearate. Such coated or uncoated metal oxide nanopigments are described in particular in patent applications EP 518 772 and EP 518 773.

The photoprotective agents are generally present in the compositions according to the invention in proportions ranging from 0.1% to 20% by weight relative to the total weight of the composition and preferably ranging from 0.2% to 15% by weight relative to the total weight of the composition.

The invention will now be illustrated by means of the non-limiting examples that follow. In these examples, the amounts are indicated as weight percentages.

EXAMPLES

Example 1

Preparation of methyltrirmethylsilyl R-2-oxo-1,3-thiazolidine-4-carboxylate

Route 1—Nucleophilic Substitution

Synthetic Scheme

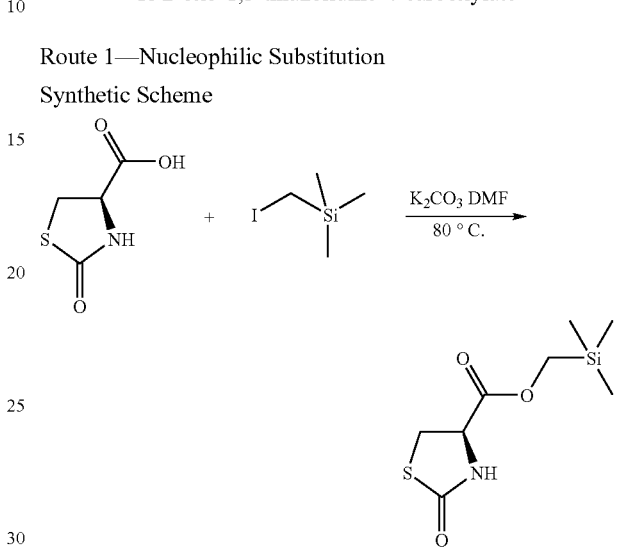

Procedure 20 g (0.136 mol, 1 eq) of R-2-oxothiazolidine-4-carboxylic acid (sold by the company Nippon Rika) are dissolved in 200 ml of N,N-dimethyl-formamide in a 500 ml three-necked round-bottomed flask equipped with a condenser. 9.4 g of potassium carbonate (0.068 mol, 0.5 eq) are added, followed by addition of 20.2 ml of commercial iodomethyltrimethylsilane (0.136 mol, 1 eq). This reaction mixture is maintained at 80° C. for 4 hours and is then allowed to cool to room temperature.

The insoluble matter of the reaction medium is filtered off on a sinter funnel of porosity 3, and the filtrate is then concentrated under reduced pressure (P=1 mbar, T=40° C.). The paste obtained is taken up in 150 ml of ethyl acetate and this organic phase is washed with 3×100 ml of water and 100 ml of saturated sodium chloride solution, and is then dried over sodium sulfate and filtered. The solvent is then evaporated under reduced pressure (P4=240 mbar, T=40° C.).

After purification of this crude product by chromatography on a column of silica, eluting with 8/2 heptane/ethyl acetate, 17.1 g of methyltrimethylsilyl L-2-oxo-1,3-thiazolidine-4-carboxylate are obtained in wax form. The yield is 54%. The NMR analysis is in accordance with the expected structure.

Route 2—Esterification

Synthetic Scheme

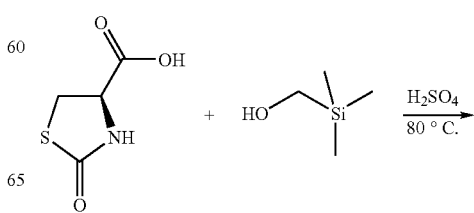

-continued

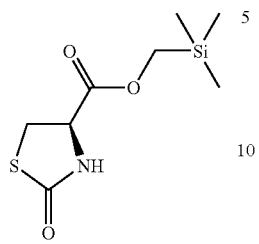

Procedure 0.2 g (1.36 mmol, 1 eq) of R-2-oxothiazolidine-4-carboxylic acid (supplied by the company Nippon Rika) is introduced into a 25 ml two-necked round-bottomed flask equipped with a condenser, followed by addition of 0.34 ml of commercial trimethylsilylmethanol (2.72 mmol, 2 eq), 0.007 ml of 98% sulfuric acid (0.13 mmol, 0.1 eq) and then 5 ml of toluene. This mixture is maintained at 80° C. for 2 hours and is then cooled to room temperature.

The reaction mixture is taken up in 50 ml of ethyl acetate and this organic phase is washed with 3×20 ml of water and 20 ml of saturated sodium chloride solution, and then dried over sodium sulfate and filtered. The solvent is then evaporated off under reduced pressure (P=240 mbar, T=40° C.).

0.28 g of methyltrimethylsilyl L-2-oxo-1,3-thiazolidine-4-carboxylate is thus obtained, in wax form, without further purification. The yield is 88%. The NMR analysis and the optical rotation are in accordance with the expected structure.

Example 2

Preparation of (4R)-2-oxo-N-[(trimethyl-silyl)methyl]-1,3-thiazolidine-4-carboxamide 2 g (0.0136 mol; 1 eq) of R-2-oxothiazolidine-4-carboxylic acid (supplied by the company Nippon Rika) are dissolved in 40 ml of dichloromethane and a catalytic amount of N,N-dimethyl-formamide in a dry 100 ml three-necked flask under argon.

The reaction mixture is cooled to 0° C. and oxalyl chloride (0.0163 mol; 1.2 eq) is then added dropwise. The reaction medium is stirred at 0° C. for 30 minutes and then at room temperature for 1 hour 30 minutes. The reaction mixture is then concentrated under reduced pressure at T=40° C. and then taken up in 80 ml of tetrahydrofuran. Trimethylsilyl-methanamine (0.0136 mol; 1 eq) and diisopropylethylamine (0.0408 mol; 3 eq) are added and stirring of the reaction medium is continued at room temperature for 20 hours.

The reaction medium is taken up in 200 ml of ethyl acetate and then washed with 3×100 ml of water and 80 ml of saturated aqueous sodium chloride solution. The organic phase is dried over anhydrous sodium sulphate, filtered and then concentrated under reduced pressure (P=240 mbar and T=40° C.).

The compound (4R)-2-oxo-N-[(trimethylsilyl)methyl]-1,3-thiazolidine-4-carboxamide is isolated by precipitation from diethyl ether. The NMR analysis, the mass spectrum and the optical rotation are in accordance with the expected structure.

Example 3

Preparation of (4R)-N-[bis(trimethyl-silyl)methyl]-2-oxo-1,3-thiazolidine-4-carboxamide (4R)-N-[Bis(trimethylsilyl)methyl]-2-oxo-1,3-thiazolidine-4-carboxamide is prepared as described in Example 2, except that the trimethylsilylmethanamine is replaced with 1,1-bis(trimethylsilyl)methanamide.

It is isolated by filtering through a pad of silica eluted with a $CH_2Cl_2$/MeOH gradient up to 98/2 and evaporating off the solvents under reduced pressure at 40° C. The NMR analysis, the mass spectrum and the optical rotation are in accordance with the expected structure.

Example 4

Preparation of 2-(trimethylsilyl)ethyl (4R)-2-oxo-1,3-thiazolidine-4-carboxylate 2-(Trimethylsilyl)ethyl (4R)-2-oxo-1,3-thiazolidine-4-carboxylate is prepared as described in Example 2, except that the trimethylsilylmethanamine is replaced with trimethylsilylethanol. The product is isolated by precipitation from $CH_2Cl_2$/pentane.

The NMR analysis, the mass spectrum and the optical rotation are in accordance with the expected structure.

Example 5

Preparation of 3-(trimethylsilyl)propyl (4R)-2-oxo-1,3-thiazolidine-4-carboxylate 2 g of R-2-oxothiazolidine-4-carboxylic acid (supplied by the company Nippon Rika) (0.0136 mol;
1 eq) are dissolved in 30 ml of anhydrous N-methyl-pyrrolidinone in the presence of potassium carbonate (0.0068 mol; 0.5 eq), and 3-chloropropyltrimethylsilane (0.015 mol; 1.1 eq) is then added. The reaction medium is maintained at 80° C. for 8 hours. The reaction medium is then cooled to room temperature and then taken up in 300 ml of diethyl ether and washed with 3×150 ml of water and then with 100 ml of saturated aqueous sodium chloride solution. The organic phase is dried over anhydrous sodium sulfate, filtered and then concentrated under reduced pressure (P=750 mbar and T=40° C.).

The 3-(trimethylsilyl)propyl (4R)-2-oxo-1,3-thiazolidine-4-carboxylate is isolated by filtering through a pad of silica, eluting with a $CH_2Cl_2$/MeOH gradient up to 98/2 and evaporating off the solvents under reduced pressure at 40° C. The NMR analysis and the optical rotation are in accordance with the expected structure.

Example 6

Method for Evaluating the Active Photo-Protection of the Derivatives of the Invention Towards UVA-Induced Oxidative Stress on Keratinocytes The technique for evaluating the photo-protection is performed according to a well-known method (J. of Photochemistry and Photobiology B: Biology 57 (2000) 102-112 TOBI et al: Glutathione modulates the level of free radicals produced in UVA irradiated cells). This technique uses a fluorescent probe as a marker of the global intracellular oxidative stress, 2',7'-dichlorofluoresceine diacetate (DCFH-DA).

Principle

The use of DCFH-DA as an oxidative stress marker is based on its physicochemical properties. It is a non-ionic apolar molecule capable of diffusing across cell membranes. Once inside the cell, DCFH-DA is hydrolysed by intracellular esterases to a non-fluorescent compound: DCFH or 2,7-dichlorofluoresceine. In the presence of activated oxygen species, DCFH is rapidly oxidized to a highly fluorescent compound: DCF or 2,7-dichlorofluoresceine.

Procedure

1. Treatment of the Keratinocytes with a Compound of formula (I)

At confluence, the keratinocytes are incubated in the presence of the compound of Example 1 for 24 hours at 37° C., 5% $CO_2$, in the culture medium, according to a dose effect (3 concentrations).

2. Incorporation of DCFH-DA

The keratinocytes, pretreated with the test compound, are rinsed and then incubated in the presence of DCFH-DA in the dark.

3. Exposure to UVA

After this incubation, the DCFH-DA solution is removed and the cells are then exposed to UVA.

Comment: an unexposed control plate is kept in darkness at room temperature.

4. Measurement of the Fluorescence

The fluorescence of the DCF is evaluated immediately after the exposure to UVA, by spectro-fluorimetry (excitation: 480 nm; emission: 530 nm).

5. Results:

The results are expressed in Table 1 below, as a % of fluorescence relative to the control cells exposed to UVA.

TABLE 1

| Compound of Example 1 (µM) | TEST 1 | TEST 2 | TEST 3 | Mean | Standard deviation |
|---|---|---|---|---|---|
| 0 | 100 | 100 | 100 | 100 | 0 |
| 100 | 95 | 81 | 75 | 84 | 10 |
| 250 | 82 | 71 | 70 | 74 | 7 |
| 500 | 75 | 70 | 58 | 68 | 8 |

The above results reveal protective efficacy of the compound of Example 1 towards UVA-induced oxidative stress according to a dose effect: the optimum efficacy is obtained at and above 500 µM (approximately 32% reduction in fluorescence).

It is thus clearly seen that the derivatives of formula (I) according to the invention induce active photoprotection of the skin relative to the untreated control.

Example 7

Comparative Study of the Photoprotective Activity of Various R-2-Oxothiazolidine-4-Carboxylic Acid Derivatives The test described in Example 6 above was performed under the same conditions on R-2-oxothiazolidine-4-carboxylic acid (Compound A) and on an alkyl derivative thereof, described in patent U.S. Pat. No. 6,004,543 (Compound B).

The results are collated in Table 2 below:

TABLE 2

| Structure | Measurement of the intracellular Red/Ox balance: % reduction in the fluorescence of the DCFH probe |
|---|---|
| Compound A | 16% at 5 mM |
| Compound (1) | 32% at 500 µM with dose effect |
| Compound B | 37% at 7 mM with dose effect |

These results show that the compounds according to the invention are much more efficient than R-2-oxothiazolidine-4-carboxylic acid and than the alkyl esters thereof, which demonstrates that the photoprotective action of these compounds is not solely attributable to their capacity to release R-2-oxothiazolidine-4-carboxylic acid.

Example 8

Cosmetic Compositions

A. Anti-Pigmenting Cream

| | |
|---|---|
| Compound of Example 1 | 1% |
| Oxyethylenated polyethylene glycol 50 | 3% |
| Mono-diglycerylstearate | 3% |
| Liquid petroleum jelly | 24% |
| Cetyl alcohol | 5% |
| Water | qs 100% |

B. O/W Emulsion for Daily Skin Photoprotection

| | |
|---|---|
| POLYDIMETHYLSILOXANE | 0.5% |
| MIXTURE OF METHYL, ETHYL, PROPYL, BUTYL AND ISOBUTYL P-HYDROXY-BENZOATES/2-PHENOXYETHANOL | 1% |

-continued

| | |
|---|---|
| STEARIC ACID | 1.5% |
| GLYCERYL MONOSTEARATE/POLYETHYLENE GLYCOL STEARATE MIXTURE | 1% |
| DEIONIZED WATER | QS |
| ETHYLENEDIAMINETETRAACETIC ACID, DISODIUM SALT, 2 H$_2$O | 0.1% |
| CYCLOPENTADIMETHYLSILOXANE | 5% |
| C$_{12}$/C$_{15}$ ALKYL BENZOATE | 15% |
| GLYCEROL | 3% |
| XANTHAN | 0.2% |
| MONOPOTASSIUM MONOCETYL PHOSPHATE | 1% |
| ACRYLIC ACID/STEARYL METHACRYLATE COPOLYMER | 0.2% |
| CETYL ALCOHOL | 0.5% |
| TRIETHANOLAMINE | 0.65% |
| MIXTURE OF CETYLSTEARYL GLUCOSIDE, CETYL ALCOHOL AND STEARYL ALCOHOL | 2% |
| COMPOUND OF EXAMPLE 2 | 1% |
| TOTAL | 100% |

C. Antisun Cream

| | |
|---|---|
| POLYDIMETHYLSILOXANE | 0.5% |
| MIXTURE OF METHYL, ETHYL, PROPYL, BUTYL AND ISOBUTYL P-HYDROXY-BENZOATES/2-PHENOXYETHANOL | 1% |
| STEARIC ACID | 1.5% |
| GLYCERYL MONOSTEARATE/POLYETHYLENE GLYCOL STEARATE MIXTURE | 1% |
| DEIONIZED WATER | QS |
| ETHYLENEDIAMINETETRAACETIC ACID, DISODIUM SALT, 2 H$_2$O | 0.1% |
| CYCLOPENTADIMETHYLSILOXANE | 5% |
| C$_{12}$/C$_{15}$ ALKYL BENZOATE | 15% |
| ETHYLHEXYL METHOXYCINNAMATE | 5% |
| GLYCEROL | 3% |
| XANTHAN | 0.2% |
| MONOPOTASSIUM MONOCETYL PHOSPHATE | 1% |
| ACRYLIC ACID/STEARYL METHACRYLATE COPOLYMER | 0.2% |
| CETYL ALCOHOL | 0.5% |
| TRIETHANOLAMINE | 0.65% |
| MIXTURE OF CETYLSTEARYL GLUCOSIDE, CETYL ALCOHOL AND STEARYL ALCOHOL | 2% |
| COMPOUND OF EXAMPLE 3 | 2% |
| TOTAL | 100% |

D. Antisun Cream

| | |
|---|---|
| POLYDIMETHYLSILOXANE | 0.5% |
| MIXTURE OF METHYL, ETHYL, PROPYL, BUTYL AND ISOBUTYL P-HYDROXY-BENZOATES/2-PHENOXYETHANOL | 1% |
| STEARIC ACID | 1.5% |
| GLYCERYL MONOSTEARATE/POLYETHYLENE GLYCOL STEARATE MIXTURE | 1% |
| DEIONIZED WATER | QS |
| ETHYLENEDIAMINETETRAACETIC ACID, DISODIUM SALT, 2 H$_2$O | 0.1% |
| CYCLOPENTADIMETHYLSILOXANE | 5% |
| C$_{12}$/C$_{15}$ ALKYL BENZOATE | 15% |
| GLYCEROL | 3% |
| TEREPHTHALYLIDENEDICAMPHORSULFONIC ACID | 1% |
| XANTHAN | 0.2% |
| MONOPOTASSIUM MONOCETYL PHOSPHATE | 1% |
| ACRYLIC ACID/STEARYL METHACRYLATE COPOLYMER | 0.2% |

-continued

| | |
|---|---|
| CETYL ALCOHOL | 0.5% |
| TRIETHANOLAMINE | 0.65% |
| MIXTURE OF CETYLSTEARYL GLUCOSIDE, CETYL ALCOHOL AND STEARYL ALCOHOL | 2% |
| COMPOUND OF EXAMPLE 4 | 2% |
| TOTAL | 100% |

The invention claimed is:

1. A compound of formula (I):

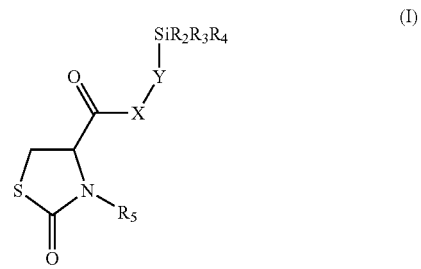

wherein:

X denotes an oxygen atom or a group NR$_1$;

Y denotes a radical (—CH$_2$)$_n$— or —CH—(SiR'$_2$R'$_3$R'$_4$)—

R$_1$ and R$_5$ independently denote a hydrogen atom a linear or branched C$_1$-C$_{20}$ alkyl group; or an acyl group whose alkyl chain contains from 1 to 10 carbon atoms;

R$_2$, R$_3$, R$_4$, R'$_2$, R'$_3$ and R'$_4$ independently denote a linear or branched C$_1$-C$_{20}$ alkyl group; and n is an integer ranging from 1 to 10.

2. The compound of claim 1, wherein the compound is in R isomer form.

3. The compound of claim 1, wherein X is an oxygen atom.

4. The compound of claim 1, wherein X is a group NR$_1$ in which R$_1$ denotes a C$_1$-C$_3$ alkyl radical.

5. The compound of claim 1, wherein X is a group NR$_1$ in which R$_1$ denotes a hydrogen atom.

6. The compound of claim 1, wherein R$_2$, R$_3$ and R$_4$ are identical or different C$_1$-C$_3$ alkyl radicals.

7. The compound of claim 1, wherein R'$_2$, R'$_3$ and R'$_4$ are identical or different C$_1$-C$_3$ alkyl radicals.

8. The compound of claim 1, wherein n is an integer ranging from 1 to 3.

9. The compound of claim 1, wherein R$_5$=H.

10. The compound of claim 1, wherein X is an oxygen atom; n=1; R$_2$=R$_3$=R$_4$=CH$_3$; and R$_5$=H.

11. The compound of claim 1, wherein the compound is selected from the group consisting of:

(4R)-2-oxo-N-[(trimethylsilyl)methyl]-1,3-thiazolidine-4-carboxamide of formula (2):

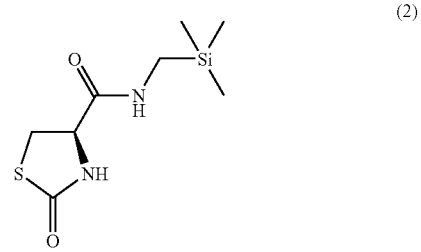

(4R)-N-[bis(trimethylsilyl)methyl]-2-oxo-1,3-thiazolidine-4-carboxamide of formula (3):

(3)

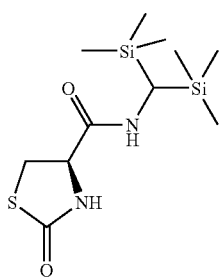

2-(trimethylsilyl)ethyl(4R)-2-oxo-1,3-thiazolidine-4-carboxylate of formula (4):

(4)

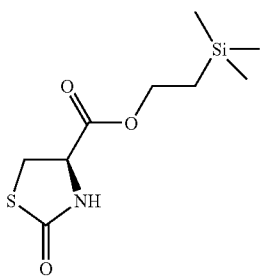

and,
3-(trimethylsilyl)propyl(4R)-2-oxo-1,3-thiazolidine-4-carboxylate of formula (5):

(5)

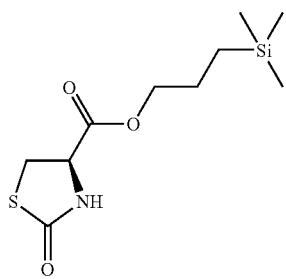

12. A composition suitable for topical application to the skin comprising the compound of formula (I) of claim 1 and a physiologically acceptable medium, wherein the compound of formula (I) is in the physiologically acceptable medium, and wherein the physiologically acceptable medium is compatible with the skin.

13. The composition of claim 12, wherein the amount of compound of formula (I) represents from 0.01 to 5% of the total weight of the composition.

14. The composition of claim 12, wherein the composition further comprises at least one compound selected from the group consisting of moisturizers, anti-pollution agents, free-radical scavengers and soothing agents.

15. The composition of claim 12, further comprising at least one organic photoprotective agent and/or at least one mineral photoprotective agent that is active in the UVA and or UVB range.

16. A method for reducing photoageing of a skin comprising applying the compound of formula (I) claim 1 to the skin in an amount sufficient to reduce the photoageing of the skin.

17. A method for preventing or reducing at least one skin condition selected from the group consisting of wrinkles, fine lines, and slackening, comprising applying the compound of formula (I) of claim 1 to a skin in an amount sufficient to reduce the at least one skin condition.

18. A method of reducing UV-induced pigmentation of a skin comprising, applying the compound of formula (I) of claim 1 to the skin in an amount sufficient to reduce UV-induced pigmentation of the skin.

19. A method for reducing photoageing of a skin, comprising topically applying to the skin a composition comprising a compound of formula (I) of claim 1 and a physiologically acceptable medium, wherein the compound of formula (I) is in the physiologically acceptable medium.

* * * * *

UNITED STATES PATENT AND TRADEMARK OFFICE
CERTIFICATE OF CORRECTION

PATENT NO. : 7,795,286 B2
APPLICATION NO. : 11/577600
DATED : September 14, 2010
INVENTOR(S) : Karine Lucet-Levannier It is certified that error appears in the above-identified patent and that said Letters Patent is hereby corrected as shown below:

Column 14, line 28, "$(SiR'_2R'_3R'_4)$–" should read --$(SiR'_2R'_3R'_4)$–;--

Column 14, line 29, "$R_1$ and $R_5$ independently denote a hydrogen atom a linear" should read --$R_1$ and $R_5$ independently denote a hydrogen atom; a linear--

Column 16, line 2, "skin comprising the compound of formula (I) of claim 1 and" should read --skin, comprising the compound of formula (I) of claim 1 and--

Signed and Sealed this

Twenty-first Day of December, 2010

David J. Kappos
*Director of the United States Patent and Trademark Office*